United States Patent [19]
Hindley et al.

[11] 4,206,145
[45] Jun. 3, 1980

[54] HYPOLIPIDAEMIC COMPOUNDS AND COMPOSITIONS

[75] Inventors: Richard M. Hindley, Reigate; Keith H. Baggaley, Redhill, both of England

[73] Assignee: Beecham Group Limited, Great Britain

[21] Appl. No.: 859,557

[22] Filed: Dec. 12, 1977

Related U.S. Application Data

[62] Division of Ser. No. 763,563, Jan. 28, 1977, abandoned.

[30] Foreign Application Priority Data

Feb. 11, 1976 [GB] United Kingdom ................. 5287/76

[51] Int. Cl.² .............................................. C07C 87/28
[52] U.S. Cl. ........................ 260/570.9; 260/340.5 R; 260/570.8 R; 424/282; 424/309; 424/310; 424/316; 424/330; 560/19; 562/433
[58] Field of Search ........................ 260/570.9; 560/19

[56] References Cited

U.S. PATENT DOCUMENTS 2,881,216   4/1959   Wright ................................. 260/570

*Primary Examiner*—Robert V. Hines
*Attorney, Agent, or Firm*—Jacobs & Jacobs

[57] ABSTRACT

Certain substituted aralkylanilines in which the aromatic aniline ring carries, at the para position to the amino function, a substituent which comprises a carboxylic acid, salt or ester, an alkyl, hydroxyalkyl, cyano or acyl group, have hypolipidaemic activity.

9 Claims, No Drawings

HYPOLIPIDAEMIC COMPOUNDS AND COMPOSITIONS

This is a division of Ser. No. 763,563 filed Jan. 28, 1977, now abandoned.

This invention relates to compounds which have hypolipidaemic activity and in particular to a class of aralkyl anilines, to a method for their preparation and to pharmaceutical compositions comprising them.

In our W. German Offenlegungsschrift No. 2,349,458, we have disclosed compounds of formula (I) as having hypolipidaemic activity:

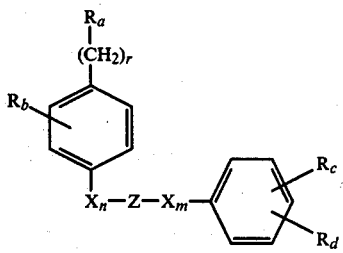
(I)

wherein $R_a$ is a carboxylic acid group or a group capable of being converted in the human body to a carboxylic acid group; $R_b$ is hydrogen, lower alkyl or lower alkoxy; $R_c$ is hydrogen, halogen, lower alkyl, or lower alkoxy; $R_d$ is hydrogen, halogen, phenyl, lower alkyl, lower alkoxyl, halo-lower alkyl, nitro or carboxylic ester group; or $R_c$ and $R_d$ together form the residue of a fused benzene ring; Z is oxygen or sulphur; X is a straight or branched chain lower alkylene, lower-alkylene-oxy, lower-alkylene-thio or lower alkylene-carbonyl group; r is zero or an integer from 1–12; and one of m and n is zero and the other is one.

We have now found a class of substituted anilines, individual members within this class having useful hypolipidaemic activity.

Accordingly, the present invention provides a pharmaceutical composition which comprises one or more pharmaceutically acceptable carriers together with a compound of formula (II), or an acid addition salt thereof:

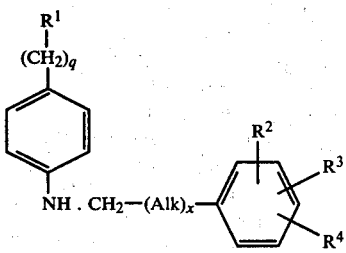
(II)

wherein $R^1$ is a carboxylic acid group or a pharmaceutically acceptable salt or ester of a carboxylic acid group; an alkyl group optionally substituted by one or more hydroxyl groups; or a cyano, or acyl group;
q is zero or an integer from 1–12;
Alk represents a straight or branched chain alkylene group;
x is zero or one;
$R^2$ and $R^3$ are the same or different and each is hydrogen, halogen, $C_{1-8}$ alkyl, $C_{1-8}$ alkoxy;
$R^4$ is hydroen, halogen, $C_{1-8}$ alkoxy, halo($C_{1-8}$)alkyl, nitro, carboxylic acid or a salt or ester thereof, hydroxy, amino, alkylamino, acylamino, phenyl; or any two groups $R^2$, $R^3$, $R^4$, on adjacent carbon atoms form the residue of a fused benzene ring.

Suitable ester groups for $R^1$ include alkyl esters, particularly lower alkyl esters. Preferred ester groups $R^1$ are methyl and ethyl esters.

The alkyl group within the definition or $R^1$ may suitably have from 1–10 carbon atoms, such as methyl, ethyl, straight or branched chain propyl, butyl, pentyl, hexyl; and may be substituted at any position with one or more hydroxy groups.

Suitable acyl groups for $R^1$ include alkanoyl groups, especially acetyl, propionyl and butyryl.

Suitably q may equal zero or an integer from 1–6, particularly 1–2.

The group 'Alk' may suitably be a $C_{1-10}$ alkylene chain more suitably $C_{1-6}$ alkylene such as methylene, ethylene, propylene, butylene. Preferably 'Alk' represents methylene.

Suitable groups $R^2$ and $R^3$ include hydrogen, chlorine, bromine, fluorine, methyl, ethyl, n- and iso-propyl n-, iso-, sec- and t-butyl, pentyl, hexyl, methoxy, ethoxy, n- and iso propoxy, n- iso, sec-, and t-butoxy, pentyloxy, hexyloxy.

Preferably one of the groups $R^2$ and $R^3$ is hydrogen.

For a compound to have maximum potential as a hypolipidaemic agent, it must significantly decrease serum lipid levels and have little or no effect on growth, liver weight and liver lipid. One class of compounds within formula (II) which has an advantageous combination of these factors has the formula (III):

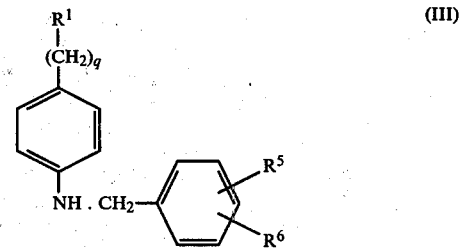
(III)

wherein $R^1$ and q are as defined with respect to formula (I), $R^5$ is hydrogen, halogen, or alkoxy and $R^6$ is hydrogen or hydroxy. Particular compounds within formula (III) wherein q is zero include:
  ethyl 4-benzylaminobenzoate;
  ethyl 4-(4-chlorobenzylamino)-benzoate;
  ethyl 4-(4-hydroxybenzylamino)-benzoate;
  ethyl 4-(4-hexyloxybenzylamino)-benzoate;
  ethyl 4-(4-hydroxy-3-methoxybenzylamino)-benzoate;
  4-(4-fluorobenzylamino)-benzoic acid;
  4-benzylaminobenzoic acid;
  4-(2-methoxybenzylamino)-benzoic acid;
  4-(4-chlorobenzylamino)-benzoic acid;
  ethyl 4-(3-chlorobenzylamino)benzoate;
  ethyl 4-(2-chlorobenzylamino)benzoate;
  methyl 4-(4-chlorobenzylamino)benzoate;
  ethyl 4-(3-bromobenzylamino)benzoate;
  ethyl 4-(2-bromobenzylamino)benzoate;
  ethyl 4-(4-methoxybenzylamino)benzoate;
  ethyl 4-(2-hydroxy-5-bromobenzylamino)benzoate;
  ethyl 4-(4-bromobenzylamino)benzoate;
  ethyl 4-(4-fluorobenzylamino)benzoate;
  methyl 4-(4-fluorobenzylamino)benzoate;

Compounds of formula (III) wherein q is an integer from 1–6 include:
4-(benzylamino)phenylacetic acid;
4-[4-(benzylamino)phenyl]-butyric acid;
4-(4-chlorobenzylamino)phenylacetic acid;
3-[(4-chlorobenzylamino)phenyl]propionic acid;
ethyl 3-[(4-chlorobenzylamino)phenyl]propionate;
methyl 3-[(4-chlorobenzylamino)phenyl]propionate;

Other compounds of formula (II) in which q is from 1–6 include:
ethyl 3-[(4-fluorobenzylamino)phenyl]propionate;
methyl 3-[(4-fluorobenzylamino)phenyl]propionate;
ethyl 3-[(3-trifluoromethylbenzylamino)phenyl]propionate;
methyl 3-[(3-trifluoromethylbenzylamino)phenyl]propionate;
ethyl 4-(3-trifluoromethylbenzylamino)phenylacetate;
methyl 4-(3-trifluoromethylbenzylamino)phenylacetate;

Another group of compounds useful in the compositions of this invention is represented by the formula (IV):

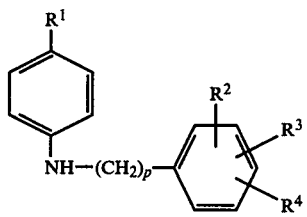

wherein $R^1$, $R^2$, $R^3$ and $R^4$ are as defined with respect to formula (II) and p is an integer from 1–6.

Specific compounds within formula (IV) in which p is 1 include:
ethyl 4-(4-methylbenzylamino)-benzoate;
ethyl 4-(4-dimethylaminobenzylamino)-benzoate;
ethyl 4-(4-carboxybenylamino)-benzoate;
ethyl 4-(1-naphthylmethylamino)-benzoate;
ethyl 4-(3-5-di-t- butyl-4-hydroxybenzylamino)-benzoate;
ethyl 4-(3,4-dichlorobenzylamino)benzoate;
ethyl 4-(3,4-methylenedioxybenzylamino)benzoate;
ethyl 4-(3,4-dimethoxybenzylamino)benzoate;
ethyl 4-(3-nitrobenzylamino)benzoate;
ethyl 4-(3-nitro-4-chlorobenzylamino)benzoate;
ethyl 4-(3-ethoxy-4-methoxybenzylamino)benzoate;
ethyl 4-(3-trifluoromethylbenzylamino)benzoate.

A specific compound of formula (IV) in which p is 2–6 is:
ethyl 4-[2-(4-chlorophenyl)ethylamino]benzoate.

A further class of compounds useful in the compositions of this invention comprises compounds of formula (II) above wherein the group $R^1$ represents an alkyl group optionally substituted by one or more hydroxyl groups, or a cyano or acyl group, and in particular such compounds in which q represents an integer from 1–12, especially 1–6.

Specific compounds falling within this sub-class when q is zero include the following:
N-4-acetylphenyl-N-4-chlorobenzylamine;
N-4-methylphenyl-N-4-chlorobenzylamine;
N-4-hydroxymethylphenyl-N-4-chlorobenzylamine;
and when q is from 1–6, the following:
N-4-acetylmethylphenyl-N-4-chlorobenzylamine;
N-4-acetylmethylphenyl-N-4-fluorobenzylamine;
N-4-acetylmethylphenyl-N-3-trifluoromethylbenzylamine;
N-4-(2-acetylethyl)phenyl-N-4-chlorobenzylamine;
N-4-(2-acetylethyl)phenyl-N-4-fluorobenzylamine;
N-4-(2-acetylethyl)phenyl-N-3-trifluoromethylbenzylamine.

The composition may be formulated for administration by any route, although an oral administration is preferred. The compositions may be in the form of tablets, capsules, powders, granules, lozenges, or liquid preparations, such as oral sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia, non-aqueous vehicles (which may include edible oils) for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa butter or other glyceride.

For parenteral administration, fluid unit dosage forms are prepared utilizing the compounds and a sterile vehicle, water being preferred. The compound, depending on the vehicle concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The composition may contain from 0.1% to 99% by weight, preferably from 10–60% by weight, of the active material, depending on the method of administration. Where the compositions comprise dosage units, each unit will preferably contain from 250 mg–3 g., of the active ingredient. The dosage as employed for adult human treatment will preferably range from 1 to 10 g., per day, for instance 3 g., per day, depending on the route and frequency of administration.

The majority of the compounds of formula (II) are novel compounds and, in a further aspect, this invention provides a compound of formula (II) above wherein $R^1$, $R^2$, $R^3$, $R^4$, q and x are as defined with reference to formula (II), with the proviso that when q is zero $R^1$ is a carboxylic acid group or an alkyl ester thereof, and $R^2$ is hydrogen, then $R^3$ and $R^4$ are not respectively
  (a) hydrogen and 2-methoxy;
  (b) hydrogen and 4-hydroxy;
  (c) 3-methoxy and 4-hydroxy; or
  (d) both hydrogen.

A preferred novel compound is ethyl 4-(4'-chlorobenzylamino)-benzoate of formula:

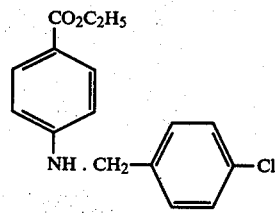

The novel compounds of this invention may be prepared by reducing a compound of formula (V):

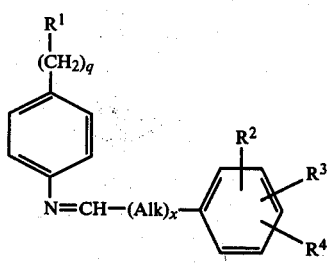

wherein $R^1$, $R^2$, $R^3$, $R^4$, q and x are as defined with respect to formula (II).

A suitable reagent to effect this reduction is a metal hydride such as sodium borohydride in an alcoholic solvent, particularly ethyl alcohol. Alternatively, catalytic hydrogenation may be employed, for example using a platinum oxide catalyst.

The intermediates of formula (V) may be prepared by reaction of an amine of formula (VI) with an aldehyde of formula (VII):

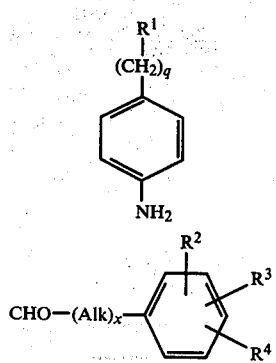

It may be convenient to generate the intermediate (V) in situ, by reacting an amine of formula (VI) with an aldehyde of formula (VII) in the presence of a reducing agent. In such a case, a suitable reducing agent is hydrogen on a platinum oxide catalyst in a suitable solvent such as a mixture of methanol and dioxan.

A second method for the preparation of compounds of formula (II) comprises reacting an amine of formula (VI) with a compound of formula (VIII):

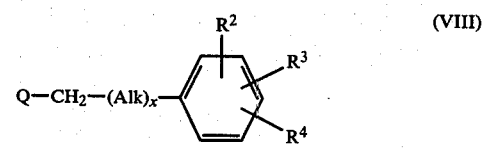

wherein Q is a readily displaceable group.

By a "readily replaceable group" is meant an atom or group displaceable by a nucleophilic centre such as the amine group of formula (VI). Such groups include halides such as iodine, bromine, or chlorine, pseudohalides, such as the azido group; active esters such as alkane- and arylsulphonyloxy groups for example methanesulphonyloxy, p-toluene-sulphonyloxy; or alkoxycarbonyloxy groups such as $O.CO.OC_2H_5$; compounds prepared in situ from dehydrating agents such as carbodiimides or carbonyliimidazoles, phosphorus pentachloride, phosphonyl chloride, thionyl chloride, phosphorus pentoxide or sulphuric acid; or other such good leaving groups.

The compounds of formula (II) may also be prepared by reduction of a compound of formula (IX):

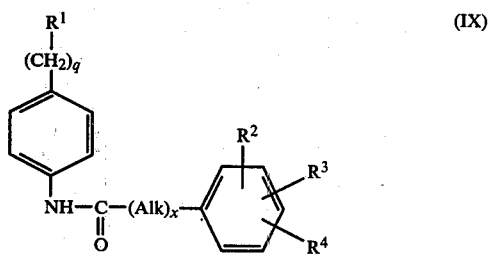

wherein $R^1$, $R^2$, $R^3$, $R^4$, Alk, q and x are as defined with reference to formula (II) above. A suitable reagent for reducing compound (IX) is borane in dimethyl sulphide.

Alternative methods of preparing compounds wherein $R^1$ contains an ester group include the esterification of the free acid or its salt or other reactive derivative of the acid, or transesterification of a compound having a different ester group. Esterification may be performed by any conventional method, for example by reaction of the free acid with the appropriate alcohol in the presence of a catalyst such as a strong acid, dry hydrogen chloride, or p-toluenesulphonic acid.

The formation of compounds (II) wherein $R^1$ is an ester may also be carried out by conventional transesterification methods, for example reaction of an ester with the appropriate second alcohol in the presence of a catalyst such as the sodium salt of the alcohol, or dry hydrogen chloride, p-toluenesulphonic acid, or potassium cyanide.

Compounds of formula (II) wherein $R^1$ is an ester may also be prepared by alkanolysis of the corresponding cyano compound ($R^1$ is $C\equiv N$); or by hydrolysis of an iminoether compound having formula (II) wherein $R^1$ is a group of formula:

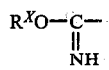

wherein $R^X$ is the hydrocarbon residue of an alcohol or phenol.

Compounds wherein $R^1$ contains a carboxylic acid group can also be prepared by the acid or base catalysed hydrolysis of the corresponding compound of formula (II) wherein R is selected from:
 (a) carboxylic acid amide group;
 (b) cyano group (—C≡N);
 (c) esterified carboxylic acid group Hydrolysis of amides may be carried out using a mineral acid as catalyst, suitably hydrochloric acid or sulphuric acid. Base catalysed hydrolysis may be carried out using an alkali metal or alkaline earth metal hydroxide, e.g. sodium or potassium hydroxide. Suitably the hydrolysis reaction is carried out in aqueous solution e.g. refluxing for several hours. The desired compound can be isolated as the free acid by neutralisation of the resultant reaction mixture or as the appropriate base addition salt (e.g. sodium salt if sodium hydroxide was employed) or acid addition salt (e.g. the hydrochloride if HCl was employed). Alternatively the free acid can be converted to any desired salt by standard procedures.

For the hydrolysis of a compound wherein $R_1$ is a cyano group, ammonia is liberated and thus the preferred catalyst is an acid which will bind the ammonia e.g. hydrogen halide such as HCl or HBr. If base catalysed hydrolysis is used, ammonia is liberated and the acid will be obtained as an alkali salt or, after neutralisation, as the free acid.

For the hydrolysis of an esterified carboxylic acid group, preferably the process involves hydrolysis with a strong base such as sodium hydroxide. The esterified carboxylic acid groups $R_1$ may be, for example lower alkoxycarbonyl groups such as methoxycarbonyl or tertiary butoxycarbonyl groups. The remarks made earlier about salts of the resultant free acid also apply in this case.

The above processes also form an aspect of this invention as do the useful novel intermediates of the formula (V) above.

Also included within the scope of the present invention is a method for controlling or reducing the serum lipid levels of mammals, including man which method comprises the administration to the mammal of one or more of the compounds of formula (II) above. An oral administration is preferred.

The compound may be administrated alone in combination with one or more pharmaceutically acceptable carriers, or as part of the total dietary intake. In the latter case, the amount of said compound employed may be less than 1% by weight of the diet and is preferably no more than 0.5% by weight. The diet for a man may consist of normal food stuffs to which the ester has been added, and similarly the diet for animals may consist of foodstuffs and the compound may be added alone or with a premix.

The following Examples illustrate this invention.

EXAMPLE 1

Ethyl-4-(4-chlorobenzylamino)-benzoate

Ethyl-4-aminobenzoate (16.5 g., 0.1 m) and 4-chlorobenzaldehyde (14.0 g., 0.1 m) were mixed in 100 ml of absolute alcohol and heated on a steam bath for 10 minutes. On cooling the product crystallised from the hot solution and was filtered and dried to give 27.5 g., of ethyl-4-chlorobenzalamino-benzoate.

This product was dissolved in 200 ml of hot ethanol and treated portionwise with 4 g of sodium borohydride with stirring. The mixture was boiled under reflux for 3 hours with stirring, cooled, poured into iced water. The solid product was filtered and dried to give 16.3 g. of ethyl-4-(4-chlorobenzylamino)-benzoate (m.p. 151° C.).

EXAMPLES 2–13

The following compounds were prepared by the method of Example 1:

| Example No. | Compound | m.p.(°C.) |
|---|---|---|
| 2. | ethyl 4-benzylaminobenzoate; | 96–7 |
| 3. | ethyl 4-(4-hydroxybenzylamino)-benzoate; | 145–6 |
| 4. | ethyl 4-(4-hexyloxybenzylamino)-benzoate; | 121–2 |
| 5. | ethyl 4-(4-hydroxy-3-methoxybenzylamino)-benzoate; | 146–7 |
| 6. | 4-(4-fluorobenzylamino)-benzoic acid | 180–81 |
| 7. | 4-benzylaminobenzoic acid; | 174–5 |
| 8. | 4-(2-methoxybenzylamino)-benzoic acid; | 168–9 |
| 9. | 4-(4-chlorobenzylamino)-benzoic acid; | 206–8 |
| 10. | ethyl 4-(4-methylbenzylamino)-benzoate; | 118–9 |
| 11. | ethyl 4-(4-dimethylaminobenzylamino)-benzoate; | 141–2 |
| 12. | ethyl 4-(4-carboxybenzylamino)-benzoate; | 240–45 (sublimes) |
| 4-(1-napthymethylamino)- | ethyl 4-(1-napthymethylamino)-benzoate. | 88 |

EXAMPLE 14

Ethyl[4-(4-fluorobenzyl)-amino]benzoate

4-Fluorobenzaldehyde (9.92 g, 0.08 mole) and ethyl 4-aminobenzoate (13.2 g., 0.08 mole) in absolute ethanol (80 ml) were boiled under reflux for 2 hours. The mixture was allowed to stand overnight at room temperature and the crystalline product was filtered, washed with cold ethanol (40 ml), 40.60 petrol (80 ml), and dried under vacuum at 40° C. The yield of ethyl 4-(4-fluorobenzal)-amino benzoate was 16.26 g.

This was dissolved in hot ethanol (100 ml) and treated portionwise with sodium borohydride (4.0 g., 0.106 mole). On completion of the addition the mixture was boiled for 30 minutes and then added to iced water (400 ml). The solid product was filtered, dried under vacuum at 70° C. and finally crystallised from absolute ethanol to give ethyl[4-(4-fluorobenzyl)-amino]benzoate (12.28 g., 56%) which melted at 109°–110.5° C.

EXAMPLES 15–30

The following compounds were prepared by the method of Example 14:

| Example No. | Compound | m.p.(°C.) |
|---|---|---|
| 15. | ethyl [4-(3,4-dichlorobenzyl)- | |

-continued

| Example No. | Compound | m.p.(°C.) |
|---|---|---|
|  | amino] benzoate | 135 |
| 16. | ethyl [4-(3,4-methylenedioxy-benzyl)-amino] benzoate | 124-5 |
| 17. | ethyl [4-(4-hydroxybenzyl)-amino] benzoate | 145-6 |
| 18. | ethyl [4-(3-chlorobenzyl)-amino] benzoate | 94-5 |
| 19. | ethyl [4-(2-chlorobenzyl)-amino] benzoate | 117-8 |
| 20. | ethyl [4-(3,4-dimethoxybenzyl)-amino] -benzoate | 131-3 |
| 21. | ethyl [4-(3-bromobenzyl)-amino] benzoate | 98-9 |
| 22. | ethyl [4-(2-bromobenzyl)-amino] benzoate | 126-7 |
| 23. | ethyl [4-(4-methoxybenzyl)-amino] benzoate | 128-9 |
| 24. | ethyl [4-(2-hydroxy-5-bromo-benzyl)-amino] benzoate | 162 |
| 25. | ethyl [4-(4-acetamidobenzyl)-amino] benzoate | 195-6 |
| 26. | ethyl [4-(3-nitro-4-chloro-benzyl)-amino] benzoate | 117 |
| 27. | ethyl [4-(3-nitrobenzyl)-amino] benzoate | 113-5 |
| 28. | ethyl [4-(4-bromobenzyl)-amino] benzoate | 148 |
| 29. | ethyl [4-(3-ethoxy-4-methoxy-benzyl)-amino] benzoate | 155-6 |
| 30. | 4-[(4-chlorobenzyl)-amino] phenylacetic acid | 155 |

EXAMPLE 31

4-[(4-chlorobenzyl)-amino]benzoic acid

4-Aminobenzoic acid (13.7 g., 0.1 mole) and 4-chlorobenzaldehyde (14.05 g., 0.1 mole) were mixed in dry benzene (200 ml.), 4-toluenesulphonic acid (50 mg.) was added and the mixture was boiled under reflux in an apparatus incorporating a water-trap until the theoretical amount of water (1.8 ml) had been collected. The reaction mixture was cooled in iced water, the product filtered, dried and hydrogenated at NTP in ethanol (500 ml) in the presence of platinum oxide, (Adams catalyst), (100 mg). The catalyst was filtered off and the solution added to iced water. The product was filtered, dried and crystallised from 20% aqueous ethanol to give 4[(4-chlorobenzyl)-amino]-benzoic acid (17.32 g., 78%) which melted at 206°-8° C.

EXAMPLES 32-34

The following compounds were prepared by the method of Example 30:

| Example No. | Compound | m.p.(°C.) |
|---|---|---|
| 32. | 4- [(4-flourobenzyl)-amino]-benzoic acid | 180-81 |
| 33. | 4- [(2-methoxybenzyl)-amino]-benzoic acid | 168-9 |
| 34. | 4- [(4-chlorobenzyl)-amino]-acetophenone | 162-3 |

EXAMPLE 35

Ethyl[4-(3-trifluoromethylbenzyl)-amino]-benzoate

Ethyl 4-aminobenzoate (8.25 g., 0.05 mole) and 3-trifluoromethylbenzyl chloride (9.45 g., 0.05 mole) were added to absolute ethanol (80 ml) containing anhydrous potassium carbonate (10 g.). The mixture was boiled under reflux with stirring for 16 hours, cooled to room-temperature and filtered. The filtrate was evaporated to dryness, triturated with ether, filtered and evaporated to dryness. The residue was chromatographed on silica-gel (400 g.) in dichloromethane to give ethyl[4-(3-trifluoromethylbenzyl)-amino]benzoate (3.82 g., 24%) melting at 69°-70° C.

EXAMPLE 36 iso-propyl[4-(4-chlorobenzyl)-amino]benzoate

Ethyl 4-(4-chlorobenzyl)-amino benzoate (7.0 g., 0.024 mole) was added to a solution of sodium (0.5 g.; 0.022 mole) in isopropyl alcohol (70 ml). The mixture was boiled under reflux for 16 hours, cooled to room-temperature and iced water was added. The solid was filtered, dried, and crystallised from isopropyl alcohol to give iso-propyl[4-(4-chlorobenzyl)-amino]benzoate (5.38 g, 74%) melting at 115° C.

EXAMPLES 37-38

The following compounds were prepared by the method of Example 35:

| Example No. | Compound | m.p.(°C.) |
|---|---|---|
| 37. | methyl 4-(4-chlorobenzyl)-amino benzoate | 125-6 |
| 38. | methyl 4-(4-flourobenzyl)-amino benzoate | 107-8 |

EXAMPLE 39

Ethyl 4-[2-(4-chlorophenyl)ethylamino]benzoate

N-(4-Ethoxycarbonylphenyl)-(4-chlorophenyl)-acetamide (8.91 g., 0.03 mole) was dissolved in dry THF (70 ml) under nitrogen and borane-dimethyl sulphide complex (3.8 ml; 0.03 mole) was added at room temperature. The mixture was stirred for 30 minutes at room temperature, boiled under reflux with stirring for 4 hours, cooled and 1 N hydrochloric acid (70 ml) was added. The organic phase was separated, the aqueous layer extracted with dichloromethane (2×80 ml), the combined organic phases washed with water (100 ml) and dried over anhydrous magnesium sulphate. Evaporation of the solvent gave an oil which was chromatographed on silica-gel (120 g.) in dichloromethane to give ethyl 4-[2-(4-chlorophenyl)ethylamino]benzoate (4.02 g, 44%) melting at 75°-77° C.

BIOLOGICAL DATA

The hypocholesterolaemic and/or hypotriglyceridaemic effects of several compounds of the present invention were demonstrated in the following experiment:

Groups of 8 male albino rats (C.F.Y. strain), weighing approximately 150 g., were given a powdered commercially available diet (oxoid) to which compounds were added at level of 0.25%. These diets were fed for seven days. The rats were then killed and their serum total cholesterol and triglyceride were measured by the Technicon Autoanalyser.

Table 1 shows the results expressed in terms of percentage cholesterol lowering and percentage triglyceride lowering compared with controls.

Table 1

| Compound of Example No. | Percentage reduction of (N.S. = Not Significant) | |
|---|---|---|
|  | Cholesterol | triglyceride |
| 1. | 27 | 46 |
| 2. | 17 | 26 |

Table 1-continued (N.S. = Not Significant)

| Compound of Example No. | Percentage reduction of Cholesterol | triglyceride |
|---|---|---|
| 3. | 21 | 54 |
| 4. | 24 | 36 |
| 5. | 7 | 50 |
| 6. | 36 | 57 |
| 7. | 32 | 60 |
| 8. | N.S. | 44 |
| 9. | 31 | 61 |
| 10. | N.S. | 27 |
| 11. | 5 | 17 |
| 12. | N.S. | 24 |
| 13. | 26 | 30 |
| 15. | 13 | N.S. |
| 16. | 41 | N.S. |
| 18. | 32 | 29 |
| 19. | 14 | N.S. |
| 21. | 22 | 62 |
| 23. | N.S. | 20 |
| 25. | 33 | 36 |
| 27. | N.S. | 34 |
| 28. | 21 | 39 |
| 29. | 21 | 25 |
| 30. | 23 | N.S. |
| 35. | 41 | 51 |
| 37. | 50 | 54 |

What we claim is:

1. A compound of formula (II) or a pharmaceutically acceptable acid addition salt:

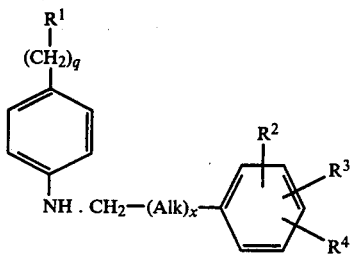

wherein:
R$^1$ is lower alkanoyl,
q is zero or an integer from 1–12,
Alk represents a straight or branched chain alkylene group,
x is zero or one,
R$^2$ and R$^3$ are the same or different and each is hydrogen, halogen, C$_{1-8}$ alkyl, C$_{1-8}$ alkoxy,
R$^4$ is hydrogen, halogen, C$_{1-8}$ alkoxy, halo (C$_{1-8}$) Alkyl, hydroxy, amino, acylamino, phenyl or any two groups R$^2$, R$^3$, R$^4$, on adjacent carbon atoms form the residue of a fused benzene ring.

2. A compound according to claim 1 wherein lower alkanoyl is acetyl, propionyl or butyryl.

3. A compound according to claim 1 wherein R$^4$ is hydrogen, halogen, C$_{1-8}$ alkoxy, halo (C$_{1-8}$) alkyl, or hydroxy, amino, alkylamino or phenyl.

4. A compound according to claim 1 wherein q is 1–12.

5. A compound according to claim 4 wherein q is 1 or 2.

6. A compound according to claim 1 wherein x is 1.

7. The compound of claim 1 which is N-4-acetylphenyl-N-4-chlorobenzylamine.

8. The compound of claim 1 which is N-4-acetylmethyl-phenyl-N-4-chlorobenzylamine.

9. The compound of claim 1 which is N-4-(2-acetylethyl)phenyl-N-4-chlorobenzylamine.

* * * * *